United States Patent [19]

Chen

[11] Patent Number: 5,242,402
[45] Date of Patent: Sep. 7, 1993

[54] SAFETY SYRINGE WITH RETRACTIBLE SELF-BIASED NEEDLE ADAPTED FOR INTRAVENOUS INJECTION

[76] Inventor: Long-Hsiung Chen, c/o Hung Hsing Patent Service Center, P.O. Box 55-1670, Taipei (10477), Taiwan

[21] Appl. No.: 16,104

[22] Filed: Feb. 11, 1993

Related U.S. Application Data

[63] Continuation-in-part of Ser. No. 952,593, Sep. 28, 1992.

[51] Int. Cl.[5] .............................................. A61M 5/00
[52] U.S. Cl. ........................................ 604/110; 604/195
[58] Field of Search ............... 604/110, 187, 195, 218, 604/220, 228

[56] References Cited

U.S. PATENT DOCUMENTS 4,804,370 2/1989 Haber et al. .......................... 604/110
5,104,378 4/1992 Haber et al. .......................... 604/110

Primary Examiner—John D. Yasko

[57] ABSTRACT

A safety syringe includes: an annular groove annularly recessed in a front surface of a plunger slidably held in the syringe to be engageable with a needle head portion formed on a rear portion of a hollow needle eccentrically mounted in a front portion of the syringe, with the annular groove having a longitudinal section formed as a biasing socket engageable with the needle head portion for biasing the needle obliquely within the syringe when retracting the plunger and the needle into the syringe, thereby preventing an outward protruding of the retracted needle for safety and hygienic purpose.

2 Claims, 4 Drawing Sheets

SAFETY SYRINGE WITH RETRACTIBLE SELF-BIASED NEEDLE ADAPTED FOR INTRAVENOUS INJECTION

BACKGROUND OF THE INVENTION

This invention is a continuation-in-part of U.S. patent application of Ser. No. 07/952,593, filed on: Sep. 28, 1992 (now granted) by the same inventor of this application.

The previously filed invention disclosed a safety syringe comprising: a syringe means (1) for filling liquid medicine (4) therein; a needle device (2) secured in a front portion of the syringe means (1) for injection use having a needle head portion (23) formed on a rear portion of the needle device (2), and a plunger means (3) slidably held in the syringe mean (1) for boosting the liquid medicine (4) in the syringe means (1) to be injected into a patient through the needle device (2) having a biasing socket (32) recessed in a front portion of the plunger means (3) engageable with the needle head portion (23) of said needle device (2) for biasing said needle device (2) obliquely within the syringe means (1) when retracting the plunger means (3) and the needle device (2) into the syringe means (1), thereby preventing an outward protruding of a retracted needle device for preventing injury or infectious contamination by the needle device (2) to environmental surroundings.

The needle device (2) of such a safety syringe is normally provided in a central portion of the syringe means (1), which is suitable for hypodermic or intramuscular injection. However, if such a syringe is used for intravenous or intravascular injection of larger quanity of liquid medicine (4) filled in the syringe cylinder (11) such as a volume of 30 cc, 50 cc, or 100 cc of the liquid medicine. The needle (2) should be eccentrically formed in the syringe cylinder for an ergonomic injection by a nurse or a doctor since the needle and the syringe cylinder can be held in a direction parallel and close to the patient's vein or blood vessels.

If the inventor's earlier application (U.S. Ser. No.: 07/952,593) is inferentially used for an intravenous injection of larger injection quanlity, the needle (2) should be eccentrically mounted in the syringe cylinder (11). Meanwhile, the single biasing socket (32) should also be eccentrically moved in order to engage with the needle head portion (23) of the needle (2). It will be very difficult and inconvenient for matching a needle head portion (23) of an eccentrically-positioned needle (2) with the single biasing socket (32).

SUMMARY OF THE INVENTION

It is therefore provided with a safety syringe including: an annular groove annularly recessed in a front surface of a plunger slidably held in the syringe to be engageable with a needle head portion formed on a rear portion of a hollow needle eccentrically mounted in a front portion of the syringe, with the annular groove having a longitudinal section formed as a biasing socket engageable with the needle head portion for biasing the needle obliquely within the syringe when retracting the plunger and the needle into the syringe, thereby preventing an outward protruding of the retracted needle for safety and hygienic purpose.

DETAILED DESCRIPTION

Figure 2:
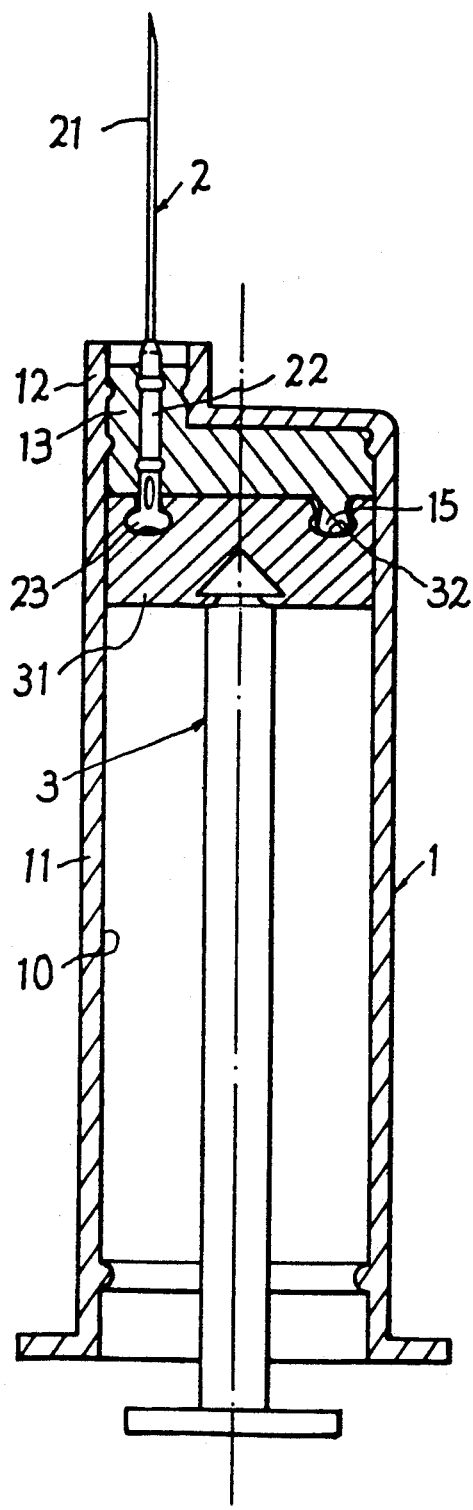
FIG. 2 shows a plunger coupled with a needle head portion of a needle device of the present invention.

As shown in the drawing figures, the present invention comprises: a syringe means 1, a needle device 2 mounted in an eccentric front portion of the syringe means 1, and a plunger means 3 slidably held in the syringe means 1 for boosting and injecting a liquid medicine 4 into a patient's blood vessel.

The syringe means 1 includes: a syringe cylinder 11 having a hollow bore portion 10 defined in the syringe cylinder 11 and a syringe axis 100 longitudinally existing in a central portion of the syringe cylinder 11, a sleeve portion 12 formed in an eccentric front portion of the cylinder 11 contracted from the cylinder 11 having a needle port 121 formed in a front opening of the sleeve 12, a front plug 13 having a plug tip portion 131 embedded in the sleeve portion 12 and a plug shoulder portion 133 embedded in a front portion of the cylinder 11 connected with the tip portion 131 and a tunnel 130 formed in the plug 13 communicating the needle port 121 for inserting the needle device 2 in the tunnel 130, a syringe handle 14 formed on a rear end portion of the cylinder 11, and a liquid-repelling extension 15 arcuately or concentrically formed on a rear surface 135 of the front plug 13 with a flat surface portion 151 disposed around the tunnel 13 recessed in the liquid-repelling extension 15 and coplanar to the rear surface 135 of the plug 13.

The plug 13 has a plurality of ring grooves circumferentially formed on the tip portion 131 and the shoulder portion 133 of the plug 13 engageable with several ring extensions 132, 134 formed in the sleeve 12 and cylinder 11 for frictionally holding the plug 13 in the syringe means 1 and also for preventing liquid leakage from the cylinder 11.

The needle device 2 includes: a needle portion 21 having a tip end 211, a hank portion 22 connected with the needle portion 21 having a plurality of needle rings 221 circumferentially formed on the shank portion 22 for firmly engaging the shank portion 22 in the tunnel 130 of the syringe means 1 for protruding the needle portion 21 beyond the needle port 121 of the syringe means 1, a needle head portion 23 formed on a rear portion of the shank portion 22 protruding rearwardly beyond a plug surface 135 formed on a rear end surface of the plug 13 to be engageable with a biasing socket of an annular groove 32 of the plunger means 3, a needle hole 20 formed through the needle portion 21, the shank portion 22 and the needle head portion 23 for passing liquid medicine 4 therethrough for injection use, a needle axis 200 longitudinally existing in a central portion of the needle device 2 normally parallel to the syringe axis 100 when eccentrically mounted in the syringe means 1, and normally aligned with a longitudinal center line of the tunnel 130 of the sleeve portion 12, and at least a venting slot 24 formed in the shank portion 22 adjacent to the needle head portion 23 for venting air outwardly through the needle hole 20 of the needle device 2.

The needle head portion 23 may be formed as elliptic shape having a needle-head center 230 intersected by a transverse head axis 230a and a conjugate head axis 230b perpendicular to the transverse head axis 230a defined in the head portion 23 elliptically shaped, with the conjugate head axis 230b of the needle head portion 23 aligned with the needle axis 200 of the needle device 2 and normally parallel to the syringe axis 100 of the syringe means 1 when the needle device 2 is normally secured on the syringe means 1.

The venting slot 24 formed in the shank portion 22 of the needle device 2 is generally elongate shaped to have a first section of a total length of the slot 24 positioned in the plug 13 and to have a second section of the total length of the slot 24 positioned beyond the plug surface 135 communicating the hollow bore portion 10 in the syringe cylinder 11. Each first section and second section of the total length of the slot 24 may be one half of the total slot length, but not limited in this invention.

The plunger means 3 includes: a plunger 31 reciprocatively held in the syringe cylinder 11, the annular groove 32 annularly recessed in a front surface portion 310 of the plunger 31 having a longitudinal section of elliptically shaped biasing socket to be operatively obliquely engageable with the needle head portion 23, a guiding port 33 formed in a front portion of the annular groove 32 converging rearwardly for communicating the annular groove 32 for slidably guiding the needle head portion 23 rearwardly through the guiding port 33 to be engaged into the biasing socket of the annular groove 32 for biasing the needle portion 21 obliquely when retracting the needle device within the hollow bore portion 10 in the syringe cylinder 11, a plunger rod 35 connected with the plunger 31 and protruding rearwardly to have a plunger-rod handle 37 formed on a rear end portion of the rod 35 for grasping the handle 37 for squeezing the plunger 31 for injection use, and a plunger axis 300 longitudinally existing in a central portion of the plunger 31 and the rod 35 aligned with the syringe axis 100. The guiding port 33 includes a front large opening 331 having a size generally equal to that of the needle head portion 23, and a rear small opening 332 rearwardly contracted from the large opening 331 and communicating the biasing socket of the annular groove 32.

Figure 3:
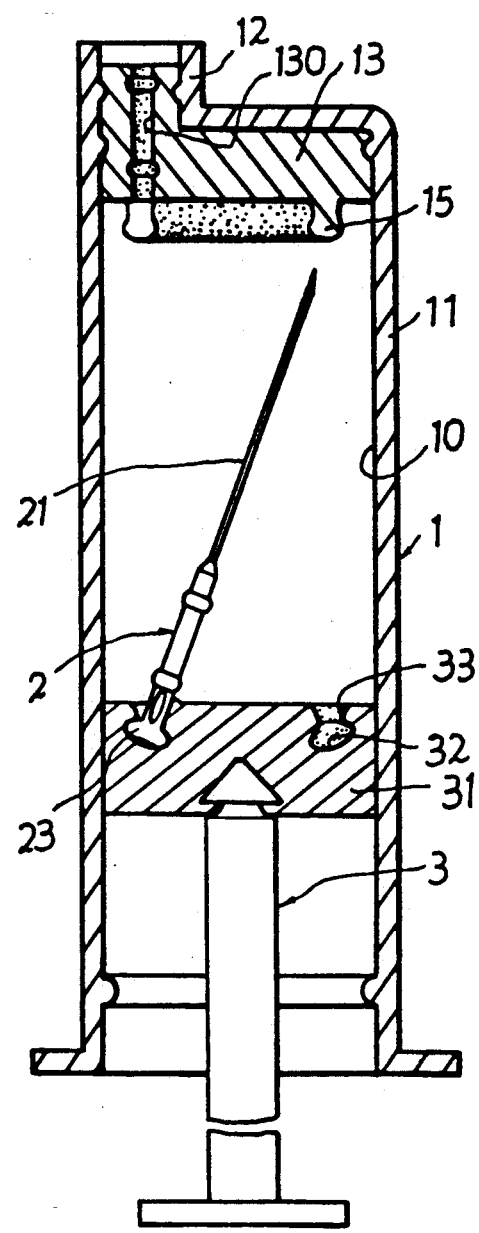
FIG. 3 shows a biased needle retracted in a syringe cylinder in accordance with the present invention.
Figure 5:
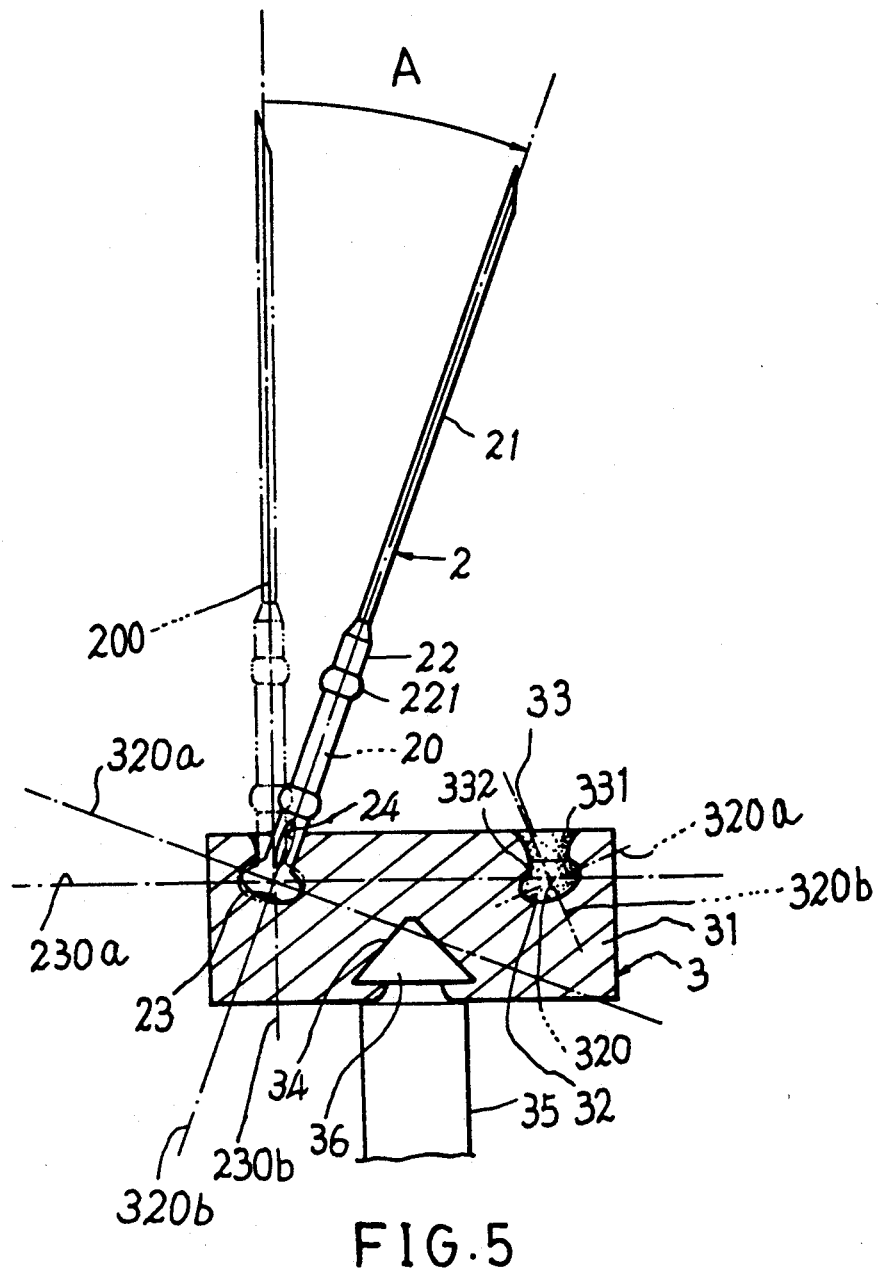
FIG. 5 is an enlarged view of the biased needle and the plunger of the present invention.
Figure 6:
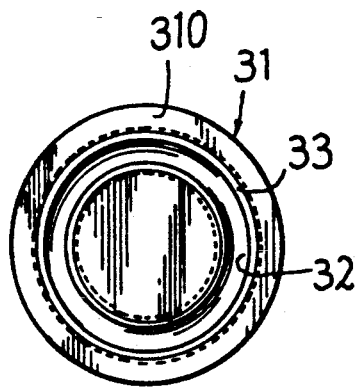
FIG. 6 is a front view of the plunger when viewed from 6—6 direction of FIG. 1.
Figure 7:
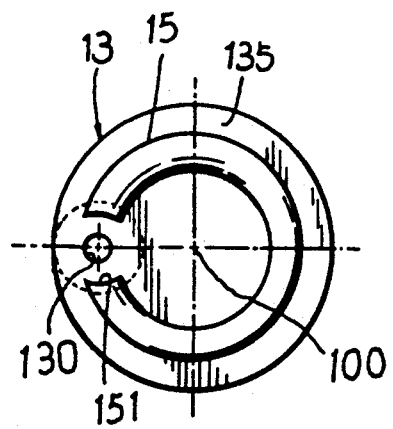
FIG. 7 is a bottom view of a front plug in the syringe cylinder when viewed from 7—7 direction of FIG. 1.

The biasing socket of the annular groove 32 of the plunger means 3 is formed as an elliptic shape having a socket center 320 intersected by a transverse socket axis 320a and a conjugate socket axis 320b perpendicular to the transverse socket axis 320a defined within the biasing socket of the annular groove 32 with the conjugate socket axis 320b normally deviated from the conjugate head axis 230b and the needle axis 20 (which is parallel to the syringe axis 100 of the syringe means 1 when the needle device 2 is inserted in the tunnel 130) for an acute angle A defined between the conjugate socket axis 320b and the needle axis 200 of the eccentrically mounted needle device 2 when retracting the needle device 2 within the hollow bore portion 10 in the syringe cylinder 11 after using the needle for medical injection purpose as shown in FIGS. 5, 3, with the socket center 320 normally aligned with the needle-head center 230 of the needle device 2 and normally aligned with the needle axis 200 when the needle device is eccentrically secured on the syringe means for intravenous injection (I.V.) purpose, whereby upon a squeezing of the plunger 31 frontwardly by pushing the rod handle 37 frontwardly to boost a liquid medicine 4 filled in the cylinder 11 for injection use through the needle hole 20, the needle head portion 23 will be engaged with the biasing socket of the annular groove 32 of the plunger 31 when the plug surface 135 matching with the plunger front surface 310 for "trans-planting" the needle head portion 23 into the biasing socket of the groove 32 of the plunger 31 (since the plunger 31 is made flexible such as from rubber material, the plunger can be compressed for a snug engagement of the needle portion 23 with the biasing socket of groove 32); and upon a retraction of the plunger 31, the needle device 2 will be retracted into the bore portion 10 of the syringe cylinder 11 and the needle-head portion 23 and the needle portion 21 will be biased with the acute angle A since the conjugate socket axis 320b of the biasing socket 32 is already deviated from the needle axis 200 of the eccentrically mounted needle device 2 with the acute angle A as aforementioned, thereby preventing a re-protrusion of the needle portion 21 outwardly from the syringe cylinder for preventing an injury or infectious contamination to an environmental surroundings.

Figure 1:
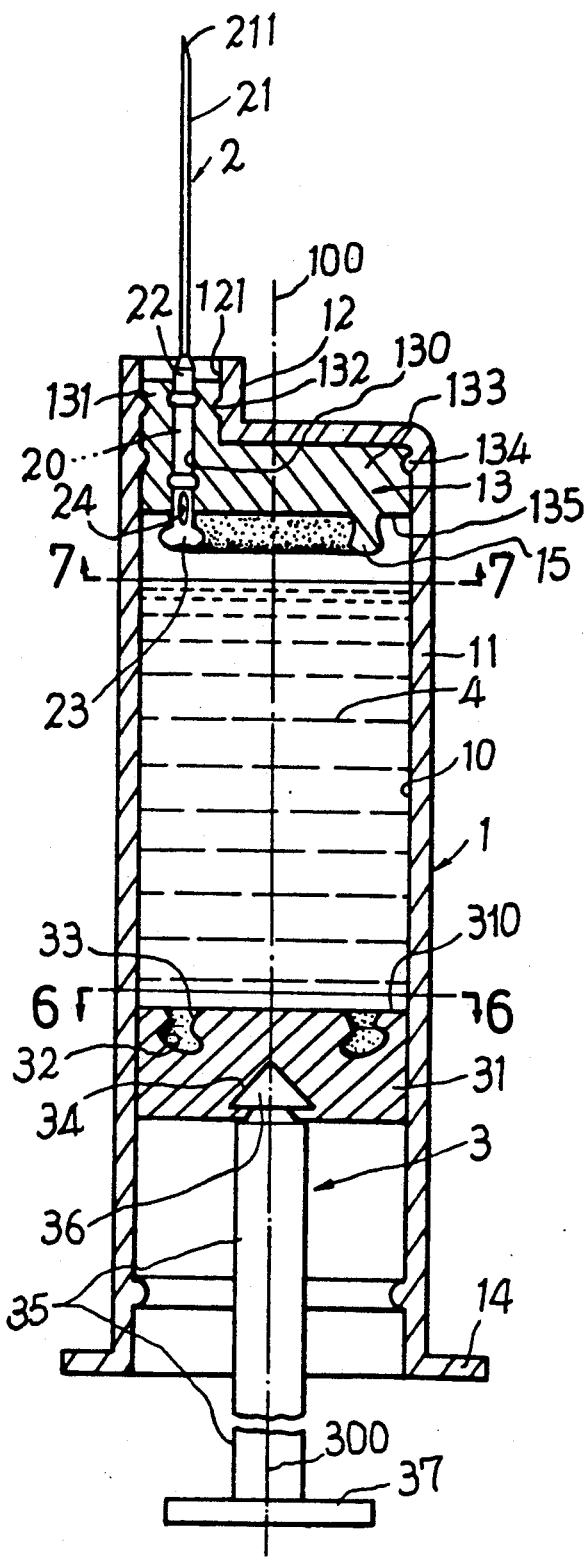
FIG. 1 is an illustration of the present invention before injection operation.

The liquid-repelling extension 15 concentrically formed in a rear surface 135 of the front plug 13 inserted in a front portion of the syringe cylinder 11 has the flat surface portion 151 recessed in the liquid-repelling extension 15 and coplanar to the rear surface 135 of the front plug 13 for receiving the needle head portion 23 of the needle device 2 within the recessed flat surface portion 151 (FIG. 1), with the liquid-repelling extension 15 having a longitudinal section of arcuate or semicircular shape and engageable with the annular groove 32 recessed in the plunger 31, thereby squeezing the liquid medicine outwardly as filled into the annular groove 32 when moving and pumping the plunger 31 towards the plug 13 for almost finishing the injecton operation for saving any medicine 4 and preventing loss of medicine even a small volume filled in the groove 32.

The liquid-repelling extension 15 has the longitudinal section of arcuate shape to be slightly smaller than the biasing socket of the annular groove 32 for an easy decoupling of the plunger 31 from the plug 13 when retracting the needle device 2 into the syringe cylinder 11 (FIG. 2 to FIG. 3).

The plunger 31 may be formed with a recess 34 in a rear surface of the plunger 31 to be engaged with a coupling member 36 formed on a front end of the rod 35 for connecting the plunger 31 with the rod 35.

Figure 4:
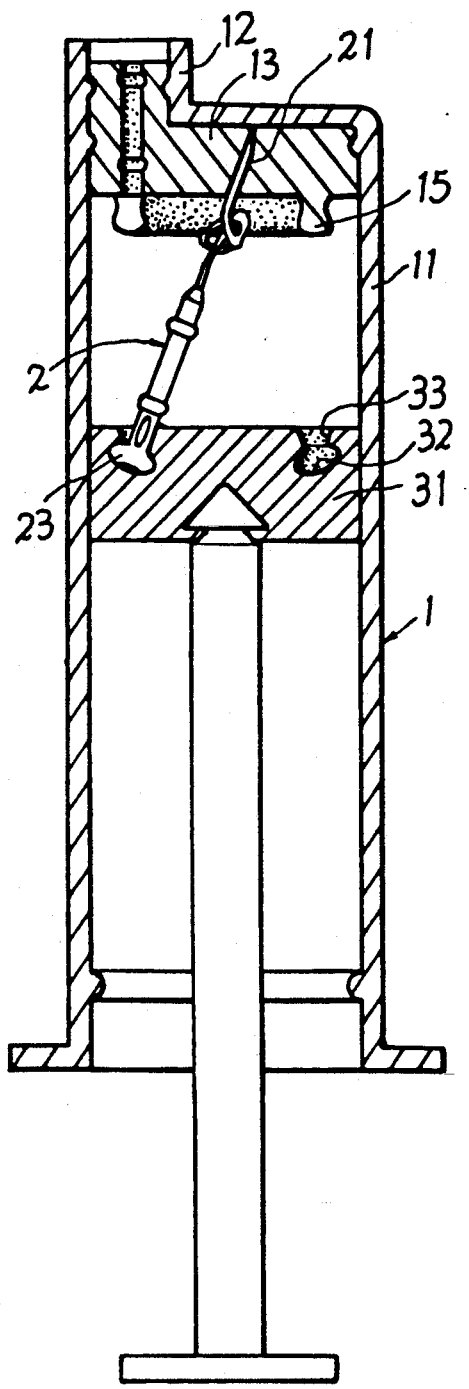
FIG. 4 shows a prevention of an outwardly protruded needle device when retracted in the syringe cylinder in accordance with the present invention.

As shown in FIG. 4, after retracting the needle 2 in the cylinder 11, a further apply of an external force for protruding the needle portion 21 outwardly, the needle portion 21 as previously biased in the cylinder 11 will be bent or even inserted into the plug 13 to be blocked by the syringe cylinder 11 to prevent its outward protrusion.

Therefore, this invention is quite safe for preventing an unexpected inadvertent protruding of an injection needle from the syringe after being used, thereby beneficial for medical or hospital waste disposal for enhancing environmental hygiene and human health. During the injection operation, the needle 2 can be transferred to the plunger 31 and retracted into the cylinder 11 without being exposed to the environment for absolute safety purpose.

I claim:

1. A safety syringe comprising:

a syringe means having a sleeve portion eccentrically formed in a front portion of a syringe cylinder of said syringe means, and a front plug embedded in the front portion of said syringe cylinder, with said syringe cylinder defining a syringe axis in a longitudinal center line of said syringe cylinder;

a hollow needle device having a needle portion formed in a front portion of said needle device normally inserted in a tunnel eccentrically formed in said front plug of said syringe means defining a needle axis in a longitudinal center of said needle device with the needle axis being parallel to said syringe axis and being longitudinally aligned with a center line of the tunnel and of said sleeve portion of said syringe means and protruding outwardly through said sleeve portion of said cylinder for injection use, and a needle head portion elliptically shaped formed on a rear portion of said needle device; and a plunger means having a plunger reciprocatively held in the syringe cylinder for boosting a liquid medicine in the syringe means to be injected into a patient through the hollow needle device, and an annular groove annularly recessed in a front surface of said plunger having a longitudinal section of said annular groove formed as an elliptically shaped biasing socket to be engageable with said needle head portion elliptically shaped of said needle device for operatively biasing said needle device in an acute angle deviated from the tunnel, whereby upon a frontward pushing of said plunger for boosting the liquid medicine in the cylinder for injection use, the needle head portion will be engaged with the biasing socket of said annular groove of the plunger; and upon a retraction of the plunger, the needle device will be retracted into the syringe cylinder and obliquely biased by said biasing socket of said plunger for preventing an outward protruding of the retracted needle device for safety and hygienic purpose.

2. A safety syringe according to claim 1, wherein said front plug in said syringe cylinder includes a liquid-repelling extension concentrically formed in a rear surface of the front plug inserted in the front portion of the syringe cylinder having a flat surface portion recessed in the liquid-repelling extension and coplanar to the rear surface of the front plug for receiving the needle head portion of the needle device within the flat surface portion, with the liquid-repelling extension having a longitudinal section of arcuate shape and engageable with the annular groove recessed in the plunger for operatively squeezing the liquid medicine outwardly as filled into the annular groove when pumping the plunger towards the front plug for finishing the injecton operation for saving any medicine filled in the annular groove.

* * * * *